US00PP36632P2

(12) United States Plant Patent
O'Brien

(10) Patent No.: US PP36,632 P2
(45) Date of Patent: Apr. 29, 2025

(54) ***LEUCOSPERMUM* PLANT NAMED 'FYNLSPPI05'**

(50) Latin Name: ***Leucospermum* hybrid**
Varietal Denomination: FYNLSPPI05

(71) Applicant: Future Fynbos Pty. Ltd., Cape Town (ZA)

(72) Inventor: Caroline O'Brien, Cape Town (ZA)

(73) Assignee: Future Fynbos Pty. Ltd., Cape Town (ZA)

( * ) Notice: Subject to any disclaimer, the term of this patent is extended or adjusted under 35 U.S.C. 154(b) by 0 days.

(21) Appl. No.: 18/445,883

(22) Filed: Mar. 1, 2024

(51) Int. Cl.
*A01H 5/02* (2018.01)
*A01H 6/00* (2018.01)

(52) U.S. Cl.
USPC ..... Plt./226

(58) Field of Classification Search
USPC ..... Plt./226
See application file for complete search history.

(56) References Cited

U.S. PATENT DOCUMENTS

PP10,644 P * 10/1998 Brits ..... Plt./226

* cited by examiner

*Primary Examiner* — Susan McCormick Ewoldt
*Assistant Examiner* — Zachariah Allan Kay
(74) *Attorney, Agent, or Firm* — Samuel R. McCoy, Jr.

(57) ABSTRACT

A new and distinct variety of *Leucospermum* plant named 'FYNLSPPI05' which is characterized by the combination of an upright growth habit, an abundance of flower-bearing main stems, conical capitula inflorescences comprised of an abundance of pink flowers with prominent vibrant pink exserted stamens, and the stability of all characteristics from generation to generation.

4 Drawing Sheets

Latin name of the genus and species: The Latin name of the genus and species of the novel variety disclosed herein is *Leucospermum* hybrid.

Variety denomination: The inventive variety of *Leucospermum* disclosed herein has been given the variety denomination 'FYNLSPPI05'.

BACKGROUND OF THE INVENTION

Parentage: 'FYNLSPPI05' is the result of a controlled cross-pollination breeding program carried out by the inventor at a commercial plant breeding facility in Cape Town, Western Cape, South Africa in September of 2012. The inventor performed a controlled cross-pollination of an unnamed, unpatented *Leucospermum lineare* plant, the seed parent, with an unnamed, unpatented *Leucospermum tottum* plant, the pollen parent. The resulting seedlings were grown for approximately two years to evaluate for new and distinct characteristics. In September of 2015, the inventor selected the new *Leucospermum* plant for its unique pink inflorescences.

Asexual Reproduction: Asexual reproduction of 'FYNLSPPI05', by way of stem cuttings, was first initiated in April of 2016 in Hopefield, Western Cape, South Africa. Through four subsequent generations of asexual propagation, the unique features of this cultivar have proven to be stable and true to type.

SUMMARY OF THE INVENTION

The cultivar 'FYNLSPPI05' has not been observed under all possible environmental conditions and the phenotype may vary somewhat with variations in environment such as temperature, day length, and light intensity, without, however, any variance in genotype. The following traits have been repeatedly observed and are determined to be the unique characteristics of 'FYNLSPPI05'. These characteristics in combination distinguish 'FYNLSPPI05' as a new and distinct *Leucospermum* cultivar:

1. *Leucospermum 'FYNLSPPI*05' exhibits an upright, freely branching growth habit with an abundance of flower-bearing stems; and
2. *Leucospermum 'FYNLSPPI*05' exhibits conical capitula inflorescences which bear an abundance of flowers with unique lime green and pink perianths; and
3. *Leucospermum 'FYNLSPPI*05' exhibits flowers with prominent bright pink exserted stamens.

BOTANICAL DESCRIPTION OF THE PLANT

Figure 1:
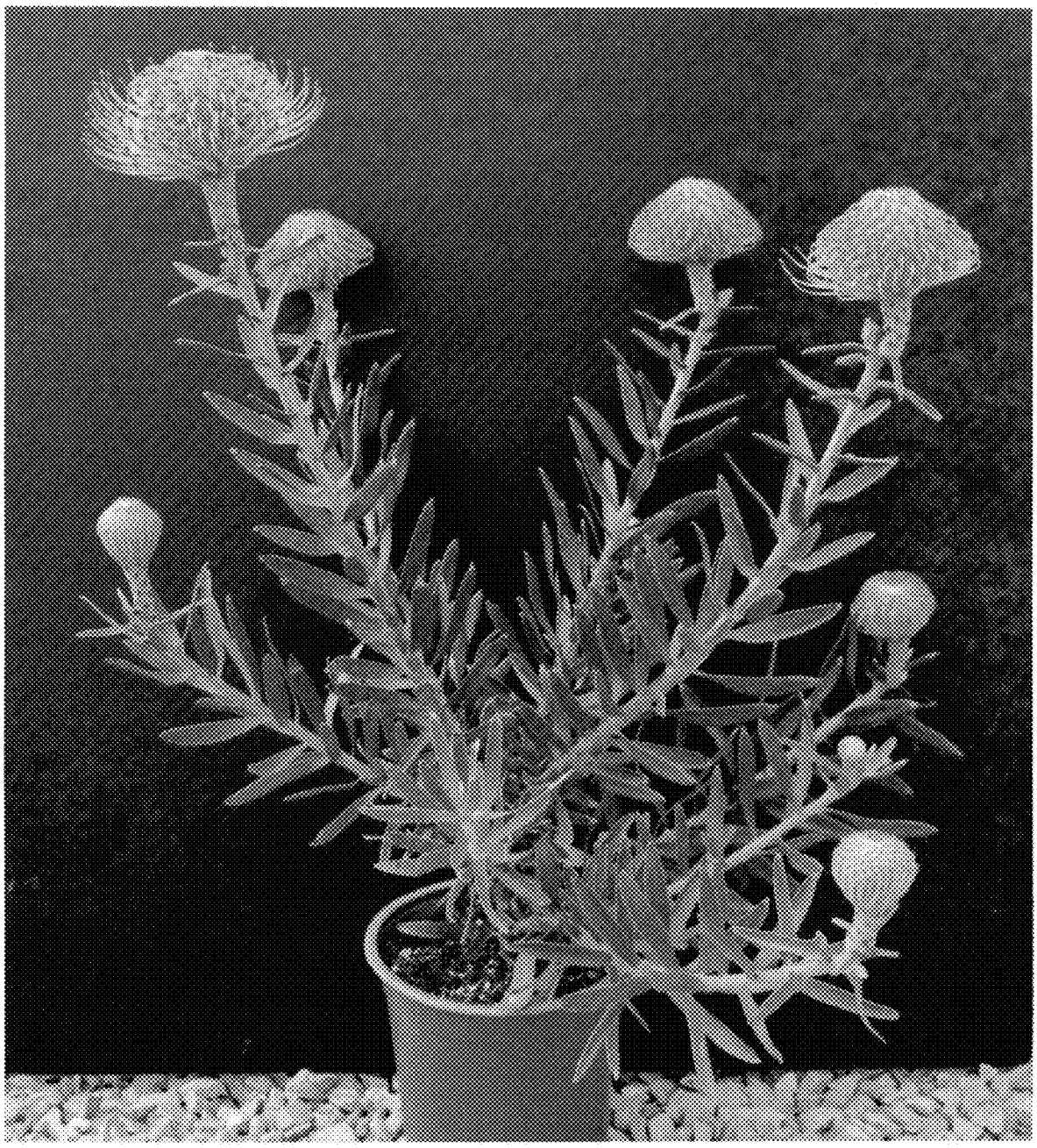
FIG. 1 illustrates, as nearly true as it is reasonably possible to make the same in color photographs of this type, an exemplary plant of 'FYNLSPPI05'. This plant is approximately 18 months old.
Figure 2:
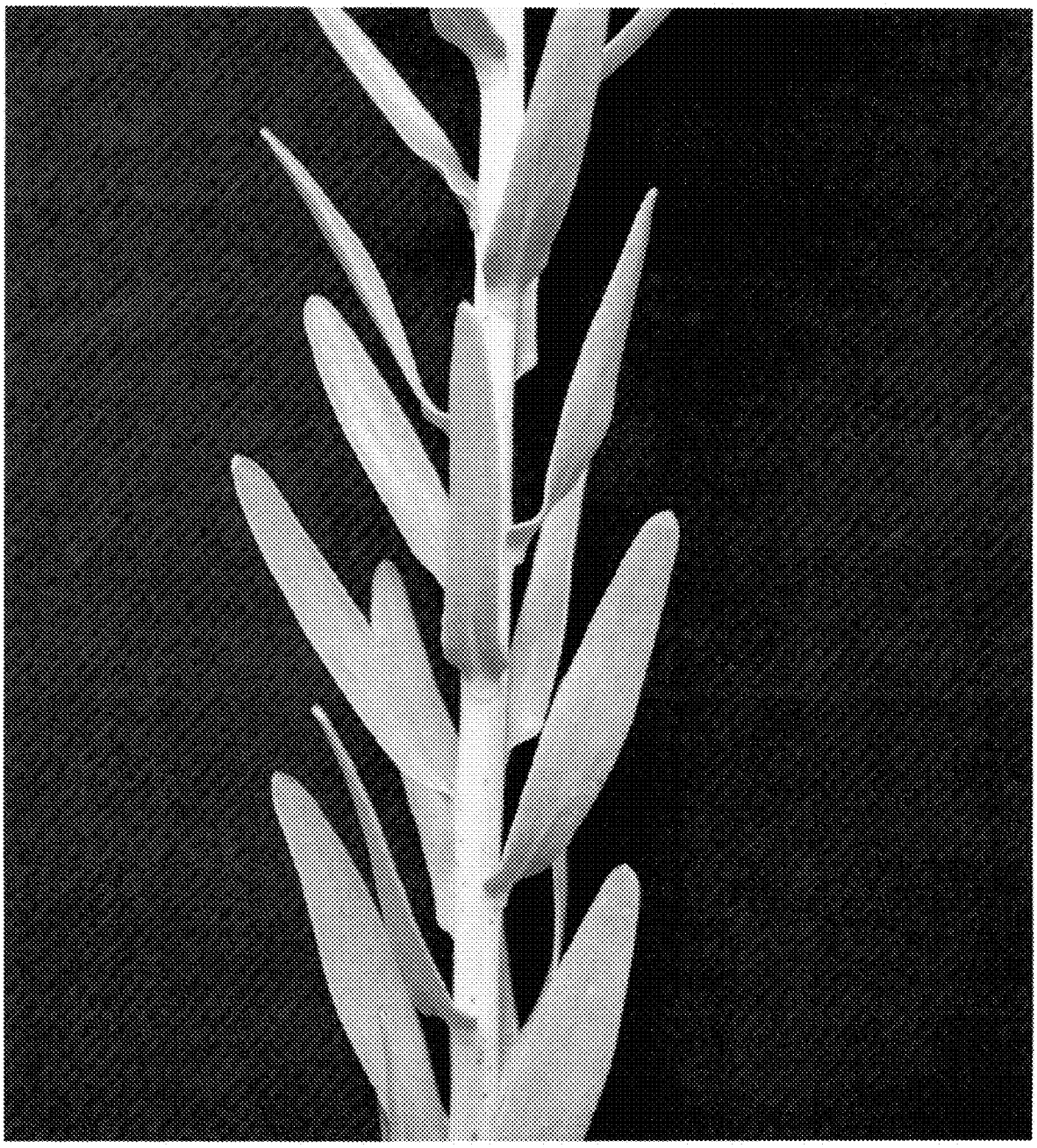
FIG. 2 illustrates, as nearly true as it is reasonably possible to make the same in color photographs of this type, the typical foliage and stem of 'FYNLSPPI05'.
Figure 3:
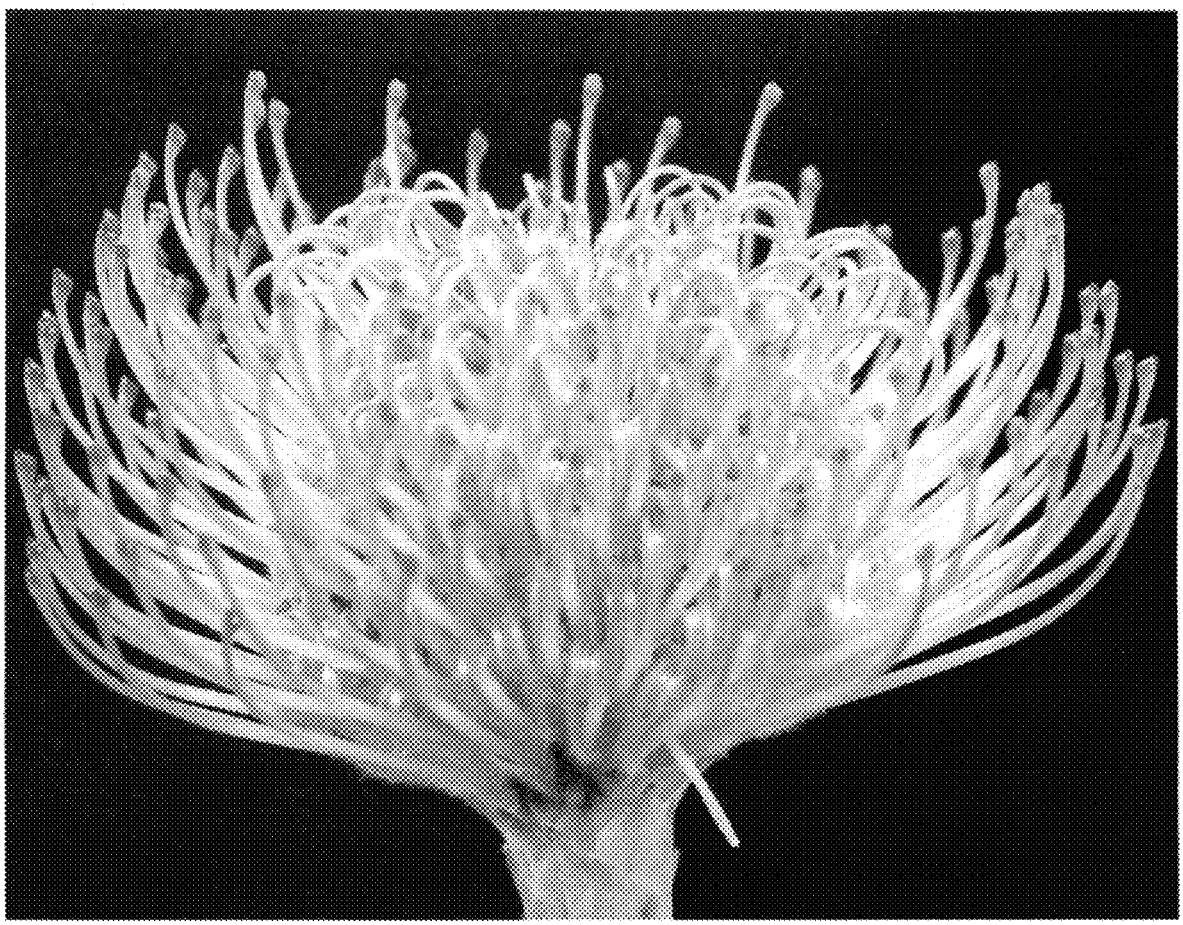
FIG. 3 illustrates, as nearly true as it is reasonably possible to make the same in color photographs of this type, the typical inflorescence of 'FYNLSPPI05'.
Figure 4:
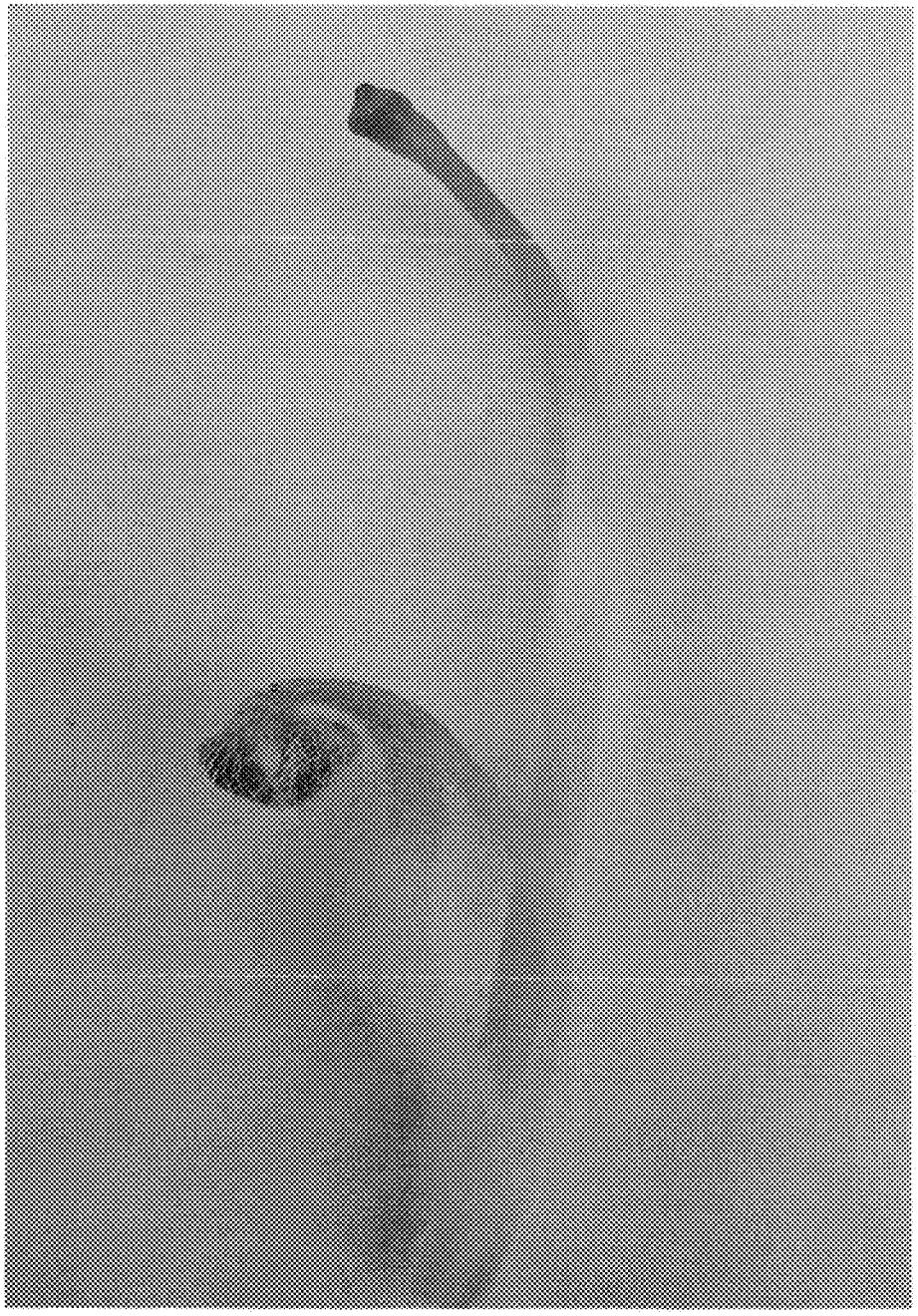
FIG. 4 illustrates, as nearly true as it is reasonably possible to make the same in color photographs of this type, the typical flower of 'FYNLSPPI05'.

The following observations and measurements were made in September of 2023 and describe 18-month-old 'FYNLSPPI05' plants grown outdoors in Piketberg, Western Cape, South Africa. Average temperatures ranged from 25 to 38 degrees Celsius during the day and 10 to 22 degrees Celsius at night during production. The plants were grown under full sun exposure and maintained with regular overhead irrigation. No pest or disease control measures were utilized in production.

Those skilled in the art will appreciate that certain characteristics will vary with older or, conversely, with younger plants. 'FYNLSPP01' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, sixth edition.

A botanical description of 'FYNLSPPI05', comparisons with the parents, and a comparison with the most similar variety of common knowledge are provided below.

General plant description:

*Growth habit*.—Evergreen shrub with an upright growth habit, with main stems bearing terminal capitula inflorescences in spring.

*Plant profile*.—Rotund.

*Height*.—50 cm, as observed; approximately 120 cm at maturity.

*Plant spread*.—40 cm.

*Propagation type*.—Stem cuttings.

*Time to initiate roots*.—Approximately 90 days at approximately 21 degrees Celsius.

*Time to produce a finished plant*.—Approximately 18 months to produce a mature, flowering plant from a rooted cutting.

*Disease resistance*.—Neither resistance nor susceptibility to typical *Leucospermum* pests and diseases has been observed.

*Environmental tolerances*.—Adapt to, at least, USDA Zones 9 through 11; high tolerance to rain; moderate to high tolerance to wind; drought tolerant once established.

Root system:

*General*.—Dense and freely branched rooting; proteoid roots.

*Distribution in the soil profile*.—Shallow to moderately deep.

*Texture*.—Smooth; glabrous.

*Color*.—Yellow-green, RHS 154D.

Stem:

*General branching habit*.—A single stem branches into multiple main stems near the base of the plant, which give rise to an abundance of lateral branches. For cut flower production, up to 30 flower-bearing stems may be harvested each year.

*Attitude of main stems*.—Upright and outward, at an approximate angle of 40 degrees from vertical.

*Quantity of main stems per plant*.—Ranging from 5 to 8.

*Quantity of lateral branches per plant*.—Ranging from 15 to 24.

*Length of lateral branches*.—Approximately 60 cm.

*Diameter of lateral branches*.—Approximately 0.7 cm.

*Internode length*.—3.0 cm, on average.

*Aspect*.—Terete.

*Texture, juvenile*.—Smooth.

*Texture, mature and oldest wood*.—Pubescent.

*Luster*.—Slightly glossy to matte.

*Strength*.—Strong.

*Color, juvenile lateral branches*.—Yellow-green, RHS 149A.

*Color, mature lateral branches*.—Yellow-green, RHS 150A.

*Color, main stem and oldest wood of lateral branches*.—Grey-brown, RHS 199B.

Foliage:

*Arrangement*.—Whorled.

*Division*.—Simple.

*Attachment*.—Sessile.

*Attitude*.—Upward and outward.

*Lamina*.—Shape — Narrowly ovate. Aspect — Flat. Dimensions — 5.0 cm long and 1.0 cm wide. Apex — Acute. Base — Cuneate. Margin — Entire; not undulated. Texture, adaxial surface — Smooth; glabrous. Texture, abaxial surface — Slightly rugose; glabrous. Luster, adaxial surface — Matte. Luster, adaxial surface — Matte. Color — Juvenile foliage, adaxial surface — Green, nearest to RHS 140A. Juvenile foliage, abaxial surface — Green, nearest to RHS 140A. Mature foliage, adaxial surface — Green, nearest to RHS 140A. Mature foliage, abaxial surface — Green, nearest to RHS 140A. Venation — Pattern — Pinnate. Color, adaxial surface — Yellow-green, RHS 149A. Color, adaxial surface — Yellow-green, RHS 149A.

*Stipules*.—None observed.

Inflorescence:

*Type*.—An upright terminal capitula with a broad, conical involucral receptacle which is subtended by multiple whorls of adpressed involucre. Flowers at the periphery of the receptacle open first.

*Natural flowering season*.—Spring.

*Time to flower or response time*.—Approximately 12 months.

*Dimensions*.—Average of 11.2 cm long and 7.6 cm in diameter.

*Quantity of flowers per inflorescence*.—200 flowers.

*Involucre*.—Quantity — Abundant; greater than 50. Shape — Deltoid. Apex — Acute to broad acuminate. Base — Truncate. Margin — Entire. Texture and luster — Glabrous; matte. Color, fully opened, lower surface — Yellow-green, nearest to RHS 149C.

Flower buds: The flower buds have not been observed.

Flower:

*Shape, type*.—Four fused tepals create a perianth tube; at anthesis the style, with a club-shaped pollen presenter at its apex, elongates and extends outward, splitting the perianth into two tepal lobes which are fused distally and reflexed; anthers are fused with the apex of the tepals.

*Attachment*.—Sessile.

*Flowering habit*.—Freely flowering.

*Attitude*.—Flowers are curled inward towards the center of the receptacle; at anthesis the styles of each flower elongate and break through the perianth tube, extending outward and away from the receptacle and inwardly-reflexed perianths.

*Flower longevity on plant*.—Approximately 14 days on the plant and as a cut flower.

*Persistent or self-cleaning*.—Persistent.

*Fragrance*.—Non-fragrant.

*Dimensions*.—5.0 cm long and 0.3 cm in diameter, at the perianth tube.

*Pedicels*.—None; flowers are sessile.

*Perianth*.—Tepals — Quantity — 4. Arrangement — Fused into a perianth tube, which is split into two lobes by the style at anthesis. Apices of tepals remain fused at anthesis. Length — 3.5 cm. Width — 0.3 cm. Apex — Fused. Base — Truncate. Margin — Entire; not undulated. Texture, inner surface — Pubescent and matte. Texture, outer surface — Glabrous and slightly glossy. Tepal color, inner surface — Yellow-green, nearest to RHS 149C, and progressively suffused with red-purple, RHS 67D, distally; red-purple, RHS 67D, at the apex. Tepal color, outer surface — Yellow-green, nearest to RHS 149C, and progressively suffused with red-purple, RHS 67D, distally; red-purple, RHS 67D, at the apex. Tepal venation color — No venation is visible. Anthers — Attachment — Basifixed to the tepals. Shape — Oblong to conical. Dimensions — 0.75 mm long and 0.5 mm wide. Texture — Pubescent. Color — A combination of yellow-green, RHS 149C, and red-purple, RHS 67D. Style — Length — 5.1 cm. Diameter — 0.2 cm at the base. Color — Yellow-green, nearest to RHS 149C, and progressively suffused with red-purple, RHS 67D, distally; red-purple, RHS 67D, at the apex, below the pollen presenter. Pollen presenter — Shape — Club-shaped. Length — 0.25 cm. Diameter — 0.25 cm. Color — Red-purple, RHS N57B. Stigma — Shape — Irregularly conical. Length — 0.15 cm. Diameter — 0.1 cm. Color — Red-purple, RHS N57B.

Seed and fruit: Seeds not observed.

COMPARISONS WITH THE PARENT PLANTS

Plants of the new cultivar 'FYNLSPPI05' differ from its seed parent, an unnamed *Leucospermum lineare* plant (unpatented), by the characteristics described in Table 1.

TABLE 1

| Characteristic | 'FYNLSPPI05' | The seed parent |
|---|---|---|
| Plant vigor | More vigorous than the seed parent. | Less vigorous than 'FYNLSPPI05'. |

TABLE 1-continued

| Characteristic | 'FYNLSPPI05' | The seed parent |
|---|---|---|
| General coloration of the inflorescence. | Pink. | Orange. |
| Natural flowering season. | Flowering earlier in the spring than the seed parent. | Flowering later in spring than 'FYNLSPPI05'. |

Plants of the new cultivar 'FYNLSPPI05' may be distinguished from its pollen parent, an unnamed *Leucospermum tottum* plant (not patented), by the characteristics described in Table 2.

TABLE 2

| Characteristic | 'FYNLSPPI05' | The pollen parent. |
|---|---|---|
| Perianth pubescence. | Less pubescent than the pollen parent. | More pubescent than 'FYNLSPP01'. |
| Inflorescence; flower abundance. | More abundant than the pollen parent, with flowers tightly held on the receptacle. | Less abundant than 'FYNLSPPI05', with flowers loosely held on the receptacle. |
| Style thickness. | Thicker than the pollen parent. | Narrower than 'FYNLSPPI05'. |

COMPARISON WITH THE MOST SIMILAR VARIETIES OF COMMON KNOWLEDGE

Plants of the new cultivar 'FYNLSPPI05' may be distinguished from the most similar known commercial comparator, *Leucospermum* 'Succession' (unpatented), by the characteristics described in Table 3.

TABLE 3

| Characteristic | 'FYNLSPPI05' | 'Succession' |
|---|---|---|
| General coloration of the inflorescence. | Pink. | Dark orange to near-red. |
| Natural flowering season. | Flowering later in the spring than 'Succession'. | Flowering earlier in spring than 'FYNLSPPI05'. |

That which is claimed is:

1. A new and distinct variety of *Leucospermum* plant named 'FYNLSPPI05', substantially as described and illustrated herein.

* * * * *